United States Patent [19]

McAfee et al.

[11] Patent Number: 5,534,252
[45] Date of Patent: Jul. 9, 1996

[54] TWO STAGE METHOD FOR THE PROTECTION OF LUMBER AGAINST SAPSTAIN

[75] Inventors: Brenda J. McAfee, Wakefield; Manon Gignac, Ottawa, both of Canada

[73] Assignee: Forintek Canada Corporation, Vancouver, Canada

[21] Appl. No.: 281,776

[22] Filed: Jul. 28, 1994

[30] Foreign Application Priority Data

Jul. 28, 1993 [CA] Canada ................................. 2101485

[51] Int. Cl.⁶ .......................... A01N 63/00; A01N 63/04; A01N 65/00
[52] U.S. Cl. .......................... 424/93.5; 264/345; 264/346; 435/252; 435/254.1; 435/267; 435/277
[58] Field of Search .................................. 264/345, 346; 435/252, 254.1, 267, 277; 424/93.5

[56] References Cited

U.S. PATENT DOCUMENTS

| 3,849,104 | 11/1974 | Daniel et al. ................... 71/65 |
| 4,419,120 | 12/1983 | Walker ........................ 71/79 |
| 4,678,669 | 7/1987 | Ricard ........................ 424/93 |
| 5,068,105 | 11/1991 | Lewis et al. .................. 424/93 |

FOREIGN PATENT DOCUMENTS

WO9301923  2/1993  WIPO.

OTHER PUBLICATIONS

Article entitled "Effect of Pasteurization On The Efficacy of Sapstain Control Products:" by A. Byrne & D. Minchin, Mar. 1992.

Boyette, C. D. 1986, Evaluation of Alternaria Crassa for Biological Control of Jimsonweed: Host Range and Virulence, Plant. Sci. 45:223–28.

Breuil, C., B. T. Luck, L. Rossignol, J. Little, C. J. Echeverri, S. Banerjee and D. L. Brown, 1992, Monoclonal Antibodies to Gliocladium Roseum, A Potential Biological Control Fungus of Sap–Staining Fungi in Wood.

Clark, J. E. and R. S. Smith, 1990, Re–infection of Pasteurized Wood With Fungi Following Storage, Forintek Internal Report Project 1712K010.

Croan, S. C. and T. L. Highley, 1990, Biological Control of the Blue Stain Fungus Ceratocystis Coerulescens with Fungal Antagonists, Mat. and Org. 25:255–266.

Klingstrom, A. E. and S. M. Johansson, 1973, Antagonism of Scytalidium Isolates Against Decay Fungi, Phytopathology, 63:473–479.

Reyes, A. A., 1984, Suppressive Activity of Different Fungi Against Cabbage Yellows in the Soil and Fusarium Oxysporum f.sp. conglutians in vitro, Phytoprotection 65:27–33.

Seifert, K. A., 1992, Sapstain of Commercial Lumber by Species of Ophiostoma and Ceratocystis, pp. 145–155 in Ceratocystis and Ophiostoma: Taxonomy, Ecology & Pathogenicity, American Phytopathological Society, Wingfield, J. J., Seifert, K. S. and Webber, J. F., eds.

Seifert, K. A., C. Breuil, L. Rossignol, M. Best and J. N. Saddler, 1988, Screening for Microorganisms with the Potential for Biological Control of Sapstain on Unseasoned Lumber, Mat. und Org. 23:81095.

Primary Examiner—Frederick Krass
Attorney, Agent, or Firm—Dressler, Goldsmith, Shore & Milnamow, Ltd.

[57] ABSTRACT

Disclosed herein is a method for controlling sapstain in wood and wood products comprising a) steam pasteurizing the wood or wood product followed by b) treating the wood or wood product with a biological control agent comprising one or more fungi selected from the class Hyphomycetes. Also disclosed are wood or wood products so treated.

14 Claims, 1 Drawing Sheet

TWO STAGE METHOD FOR THE PROTECTION OF LUMBER AGAINST SAPSTAIN

BACKGROUND OF THE INVENTION

Wood is a biodegradable material which, at moisture contents ranging from 20–40% (Colley & Rumbold 1930, Cartwright and Findlay 1958, Soderstrom 1986), is susceptible to fungal attack. Sapstain is the name given to the greyish, blackish or blueish discolouration of the sapwood resulting from the presence of pigmented fungal hyphae that penetrate along the medullary ray cells. Sapstain fungi utilise the easily assimilable nutrients in the wood leaving the structural carbohydrates. Sapstain is thus considered to be an aesthetic problem causing negligible loss of biomass or strength properties of the wood. The presence of these fungi in the wood, however, creates favourable conditions for infection of decay fungi and some sapstain fungi have been known to cause soft rot (Wang & Zabel 1990).

Three broad groups of fungi are associated with sapstain; 1) Ophiostomatalean fungi including species of Ceratocystis, Ceratocystiopsis and Ophiostoma, 2) Black yeasts such as *Hormonema dematioides, Rhinocladiella atrovirens, Aureobasidium pullulans, Leptodontidium elatius*, and Phialophora spp. 3) Dematiaceous moulds such as *Alternaria alternata* and *Cladosporium cladosporoides* (Seifert 1992). Growth of other surface moulds such as Penicillium and Trichoderma spp, while frequently producing abundant green conidia on wood, discolours only the surface of the wood and can be easily removed by planing.

Sapstain fungi can be controlled by protective chemicals. In British Columbia, Canada alone, mill practices involve the annual treatment of 3.6 million board feet of lumber with a value in excess of Can. $2 billion (Gilbert 1988). Without chemical treatment, a significant portion of high value lumber must be sold in lower value markets at an estimated potential cost to the British Columbia lumber industry of Can. $388 million per annum (Deloitte et al, 1989). For over 50 years the industry relied on chlorinated phenols to control fungal growth but concerns over carcinogenicity, fish toxicity and the presence of potential dioxin contaminants resulted in discontinuance the use of these chemicals (Bray 1981, Jones 1981). Most of the alternative chemicals are not as universally effective as the chlorinated phenols (Miller & Morrell 1989, Miller et al, 1990) and also result in high fish toxicity, eye and skin sensitivity (Henderson 1992, Hanssen et al, 1991) corrosion of equipment, unwanted discoloration of wood and increased costs (Gilbert 1988).

One of the long term objectives of the sawmill industry is to eliminate the use of toxic substances for the protection of lumber against stain, mould and decay. There has been much interest in biological control for agriculture applications, and some products have been registered (Lewis et al, 1991). However, the majority of efforts have shown that biological control is both less efficacious and more variable than control obtained with chemical agents (Harman and Lumsden 1990). A principal reason for these suboptimal results is the poor germination and growth of the biocontrol agent.

A number of biological control organisms (bioprotectants), including bacteria, mycorrhizal fungi, decay fungi and other sapwood inhabiting fungi have been investigated Benko 1988, 1987, Selfeft et al, 1988, Croan & Highley 1990, Morrell & Sexton 1992) but no successful applications in wood have been developed. Several strains of the genus Gliocladium have been reported to have utility in the protection of lumber against sapstain on small blocks of wood, for example in Applicant's Patent Cooperation Treaty application number PCT/CA92/00299 that was published under number WO 93/01923 on Feb. 4, 1993.

The mechanisms by which biological control organisms (bioprotectants) achieve control are thought to be through interference competition (mycoparasltism, inhibitory or toxic metabolite production) or by exploitation competition (competition for nutrients). The microbial community (or microflora) of lumber is composed of populat ions of fungi, yeasts, bacteria and actinomycetes. The species composition of the microflora is a result of the nutrient availability in the substrate as well as climate and seasonal factors, substrate species and the spores circulating in the air surrounding the lumber. The interact ions between an introduced bioprotectant isolate and the existing community will be strongly influenced by all of the above factors. Any method of controlling sapstain in lumber will have to take into account the presence of the microbial flora in the lumber in order to be effective.

Another recognized problem with wood products in several countries is the presence of the pinewood nematode (PWN). In Japan the PWN has been shown to be responsible for pine wilt disease (Mamiya and Kiyohara. 1972), resulting in destruction of some plantation grown pine species. Pine wilt disease has never been recognized as occurring in Canada's forest, where the necessary conditions for the development of this disease do not seem to occur (Rutherford et al 1990). The PWN also occurs in China (BaoJun and Quoli 1989), Taiwan and Korea. The European Community (EC) believes that the PWN does not occur in Europe. Since the EC is very dependent on the importation of lumber and timbers, particularly from North America, they have become very concerned about the potential introduction of PWN to Europe. Canada has been very responsive to the EC concerns and has, over the years, implemented measures to dramatically reduce the risk of exporting PWN. A very strict lumber grading inspection program known as the Mill Certification Program for Bark and Grubhole Control (MCP), has been implemented. Through this program, sawmills and shippers guarantee that all bark and grubholes have been eliminated from the lumber. It is worth noting that following almost 100 years of lumber shipments and 200 years of round wood shipments such as masts as spars, from North America to the EC, even without the MCP in place, no evidence of pine wilt disease has been found in Europe.

In view of the above problem with pinewood nematodes, the Applicant was commissioned by Forestry Canada to lead a research initiative to examine pasteurization as an alternative to kiln drying for the eradication of the PWN from lumber.

Pasteurization uses temperatures lower than those required for sterilization, resulting in the killing of select-organisms. It can be used where higher temperatures may be detrimental to the materials being heated, as for example in the pasteurization of milk or in the brewing industry. It has been used to control a range of microorganisms in various materials, including nematodes in soil (Todd and Pearson, 1988). The use of simple and clean, wet heat, is very attractive and presents no direct environmental problems. It is a well established fact that PWN (Dwinell 1990) and beetles (Ostaff and Cech. 1978), like most organisms, can be killed by moderate heat, but for Canadian lumber species little data exists on what temperature would be required, or for how long.

Applicant determined that the pasteurization of unseasoned coniferous wood under laboratory conditions using wet heat at 56.1° C. for 30 minutes, resulted in total mortality for PWN with a reliability of 99.994% with 95% confidence. This conclusion was derived for the worst conditions of PWN isolate, wood species and moisture content of those tested.

Pasteurization of unseasoned lumber, using an operational temperature of 56° C. for 30 minutes, was demonstrated at three different locations across Canada using a conventional, high temperature, and dehumidification kiln. No surviving PWN were found in the lumber treated at any of the three locations. This clearly demonstrated the applicability of pasteurization under mill conditions using a temperature slightly above that found to be necessary under laboratory testing.

However it was recognized that before pasteurization could be applied to industrial lumber production its deleterious effect on the antisapstain formulations used to protect lumber in transit and storage would have to be evaluated. In a study by Clark and Smith (1990) it was determined that lumber that has been pasteurized is more susceptible to re-infection and discoloration by staining and mold fungi than wood that has not been pasteurized. The authors therefore concluded that pasteurized wood will require antisapstain treatment to prevent degradation by stain, mold and decay fungi.

A recent study by Byrne and Minchin (1992) clearly shows the magnitude of this problem and its specificity to individual formulations. In particular they noted that pasteurization reduced the efficacy of chemical ant i-sapstain agents and concluded that pasteurized wood was a greater challenge to sapstain control.

SUMMARY OF THE INVENTION

The present invention relates to a process for the protection of unseasoned lumber against undesirable sapstain using a combination of pasteurization and a biological anti-sapstain agent.

In particular, the present invention provides a method for controlling sapstain in wood and wood products comprising;

a) steam pasteurizing the wood or wood product lumber; and b) subsequently treating the wood and wood product with a biocontrol agent comprising one or more fungi selected from the class Hyphomycetes.

Contrary to what others have found or predicted, pasteurization of the wood prior to administering the biological anti-sapstain agent actually increased the efficacy of the biological agent.

The pasteurization of the lumber has been shown to reduce the level of fungi that normally compete with Gliocladium and which reduce the efficacy of Gliocladium when used alone. Consequently, immediately after pasteurization the wood is in a form very amenable to the growth of the anti-sapstain agent, In a preferred embodiment, the wood is pasteurized for a period of time of not less than 30 minutes such that the internal temperature of the wood reaches at least 56° C.

The biological control agent is one that can substantially reduce the levels of sapstain in the wood or wood product so that it is commercially acceptable. Fungi from the class Hyphomycetes have demonstrated antagonistic reactions to other fungi and the potential to control plant diseases as well as weed species. Genera from the class Hyphomycetes that have demonstrated such activity includes Gliocladium (Seifert et al 1988), Trichoderma (Mukhopadhyay et al 1992), Penicillium (Reyes A.A. 1984), Colletotrichum (Daniel et al 1974) and Alternaria (Boyette, C. D. 1986), Fusarium (Walker, H. L. 1983) and Curvularia (Nielsen et al. 1992).

In a preferred embodiment, the biocontrol agent used is *Gliocladium aureum* 784A (deposited in the American Type Culture Collection under no. ATCC 10406). However, other strains of Gliocladium that are effective in controlling sapstain may also be used. Examples of such strains include *Gliocladium roseum*, such as *Gliocladium roseum* 321M (deposited at the University of Alberta Microfungus Collection and Herbarium under no. UAMH 419); *Gliocladium roseum* 321A (deposited at the US Army Natick Labs, Natick Mass under no. A P18-13); *Gliocladium roseum* 321B (deposited at the US Army Natick labs., Natick Mass under no. AP17-3); *Gliocladium solani* 810A (deposited in Centraalbureau voor schimmelcultures CBS 187.29); *Gliocladium virens* 258C (deposited in the American Type Culture collection under no. ATCC 9645); and *Gliocladium virens* 258D (deposited at the University of Technical Sciences, Budapest XI, Hungary under number BKMK 1117).

It is to be noted that the numbers used to identify the Gliocladium species in the present application are the numbers that the Applicant, FORINTEK Canada Corp. uses in their culture Collection. Samples of any of the isolates referred to are available upon request to Forintek Culture Collection of Forintek Canada Corp., 800 Montreal Road, Ottawa, Ontario, Canada K1G 3Z5.

The method of the present invention has many advantages. Firstly, it reduces the levels of sapstain in the wood to make it commercially acceptable. Secondly, the anti-sapstain treatment does not employ chemicals which are harmful to the environment. Thirdly, by pasteurizing the wood, pinewood nematodes that may be present are eliminated. The latter may be required for any wood exported into Europe. Consequently, by a single procedure two important problems can be solved.

DETAILED DESCRIPTION OF A PREFERRED EMBODIMENT

Figure 1:
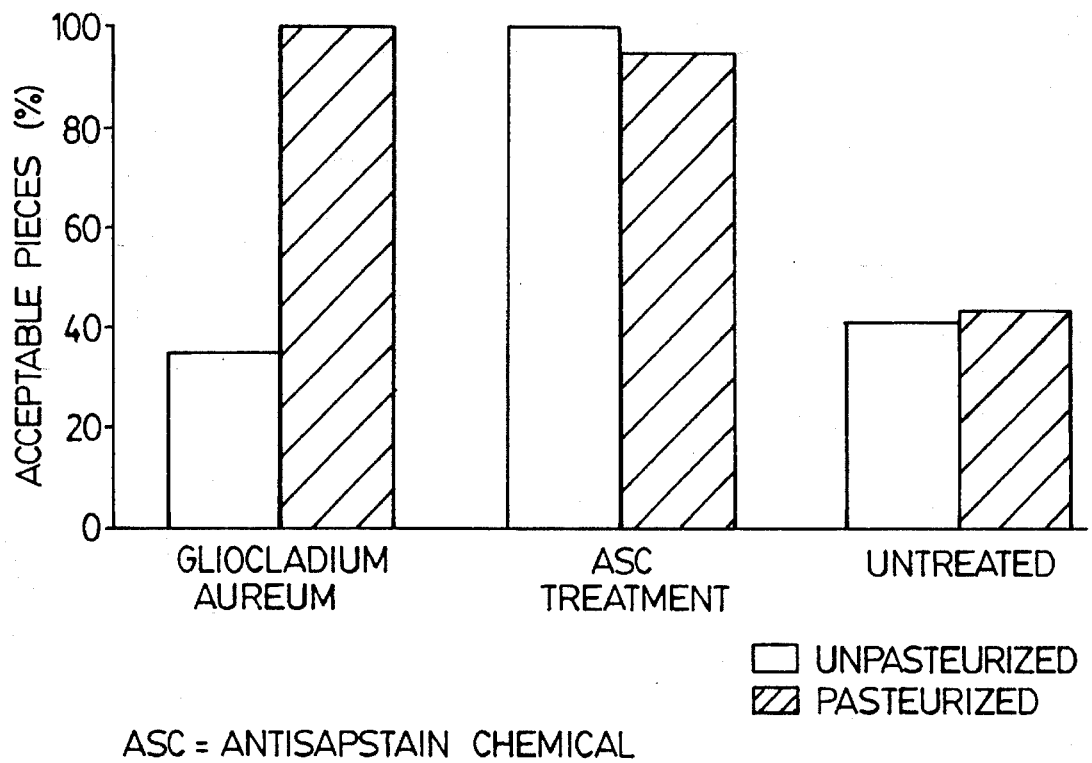
FIG. 1 is a graph illustrating the % acceptability of pieces of lumber after three months of various treatments as outlined in the disclosure.

The present invention will be described in greater detail with reference to the following example.

Methods

Untreated, green 2×4 hemlock lumber from a British Columbia sawmill was sawed in lengths of 15 inches. The samples were assigned one each of six treatments, A) chemically treated and pasteurized, B) chemically treated only, C) pasteurized only and D) untreated, non pasteurized control, E) treated with biological control agent and pasteurized, F) treated with biological control agent only. All samples were stored at −25° C. until utilization.

Chemical anti-sapstain treatment was applied as a dip for 15 seconds in a 1:80 dilution of the product in water. The product chosen as reference for this study contains didecyl dimethyl ammonium chloride (DDAC) (64.8%) and 3-iodi-2-propynyl butyl carbarate (7.6%) as active ingredients (72.4% A.I.) and is commonly used as reference product in sapstaining trials (Rusternburg and Klaver 1992). Neutron Activation Analysis was carried out on punched samples from the dipped boards to verify that the target retention levels recommended by manufacturers (90ug/cm$^2$ DDAC) were satisfied (Byrne and Minchin 1992).

The wood samples were pasteurized in a drying kiln, providing a thermal death time for pine wood nematodes of 56° C. for 30 minutes (Cook et al, 1993). Heat was supplied by live steam to achieve a maximum air temperature of 85° C. after 2 hours and this temperature was maintained for 4 hours. After about 2 hours the maximum internal wood temperature measured was approximately 80° C. and the minimum internal wood temperature was approximately 56° C. To prevent the lumber from drying, a saturated atmosphere was maintained. To prevent moisture loss from the wood during the heat treatment, the ends were covered with silicone, which was then removed prior to incubation.

The treatment with the biological control agent consisted of inoculation with a spore solution of the fungus *Gliocladium aureum* (784A) at a concentration of $10^5$ spores mL$^{-1}$. The samples were subjected to a 15 second dip in a small dip tank containing five liters of spore solution. Wood samples were placed on a draining rack, allowing excess solution to run off before being placed in incubation boxes.

The wood was incubated in covered plastic boxes 61.0× 40.6×41.9 cm. Ten holes (0.25 cm in diameter) punched in the top and sides were covered by 0.2 μm filters to enable air exchange while controlling spore entry. In each box, sterile distilled water (750 ml) was added to maintain a high relative humidity during the incubation period. The wood pieces in each box rested on four petri dishes to avoid direct contact with water. The boxes were incubated in an environmentally controlled chamber set at 20° C. and 65% relative humidity.

Ten to twelve wood samples were assigned to each box depending on the wood species. Each treatment consisted of four replicate boxes with samples randomly assigned per box.

Boxes were opened for inspection of wood pieces after three months and six months incubation. Pieces were individually rated for mould, stain, and decay and for acceptability of sapwood discolouration. The ratings were based on a 0 to 5 scale where, 0=no growth, 1=trace of fresh fungal growth, 2=little fresh fungal growth, 3=moderate amounts of fungal growth, 4=heavy fungal growth, 5=very heavy fungal growth. A rating was done on all four surfaces of each sample and the results averaged for the entire sample. Consideration was given to both the surface area covered and the intensity of growth and discolouration. Using this scale the percentage of "acceptable" pieces was determined. A score of 2 or less is considered to be commercially acceptable and approximates the level which would be acceptable on a 2×4 construction commodity in most overseas markets.

The results after three months were analyzed using n-way Contingency table analysis. The Chi-squared test for independence was used to determine significant differences among treatments. The Breslow-Day test (Breslow and Day 1980) was used to test the homogeneity of the odds ratios.

Results

Chi-squared contingency analyses revealed that after 3 months incubation in controlled environmental conditions, chemical treatment was significant (p<0.0001) and independent of pasteurization for control pieces; showing a 2.2 (95%C.I.=1.5,3.0) and a 2.4 (95%C. I.=1.7,3.4) times greater likelihood of acceptability for pasteurized and unpasteurized wood pieces respectively. Pasteurization did not show a significant effect for control pieces (p=0.872). The combination of G. aureum biological control agent with pasteurization resulted in 2.3 times higher acceptability levels (95%C. I.=1.7, 3.2, P21 0.0001) as compared to wood samples that were not pasteurized (p=0.529).

The treatment consisting of the biological control agent *G. aureum*, applied directly after pasteurization, resulted in acceptability levels (100%) for stain equal to those obtained with chemicals (100% when not pasteurized and 95% when pasteurized) and within the range of the industrial standard (95%). These values are graphically represented in FIG. 1.

After six months incubation, *G. aureum* treated lumber pieces showed 92% acceptability when pasteurized and 21% when the pasteurization process was not included. Acceptability levels of the *G. aureum* treated and pasteurized lumber compare favourabillty with the sapstain chemical treatment where chemical treatment alone gave acceptability levels of 98% while for the chemically treated and pasteurized lumber acceptability was at 65%.

Figure 2:
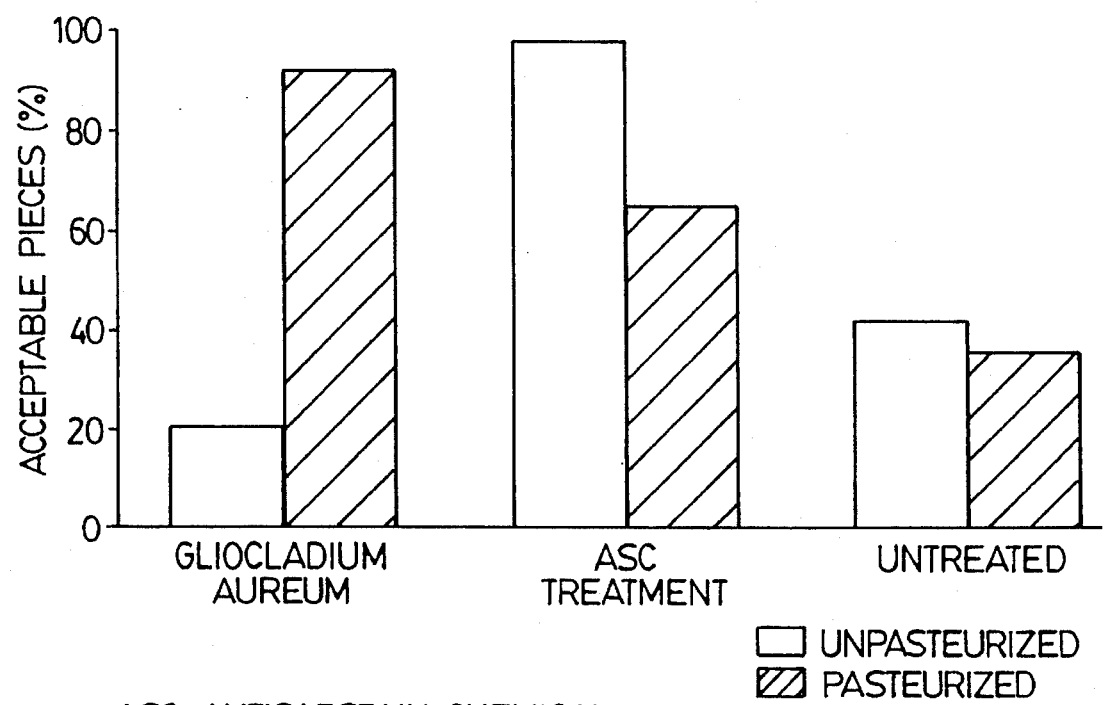
FIG. 2 is a graph illustrating the % acceptability of pieces of lumber after six months of various treatments as outlined in the disclosure.

Untreated controls had 40% of the pieces acceptable after 6 months while untreated pasteurized pieces shown 35% acceptability. The results are show in FIG. 2.

The implications of these results are important as they are the first promising indications that biological control of sapstain in unseasoned softwood lumber may be feasible on full size lumber. The results also indicate that pasteurization prior to inoculation with the biological control agent exerts a selective pressure on the wood by decreasing levels of microflora which would, under normal conditions, compete with the biological control agent and reduce its efficacy. Therefore, it is reasonable to predict that other forms of selective pressures applied to the competing microflora may also lead to improved efficacy of the biological control agent. For example applying nutrients to the wood that selectively enhance the growth of the biological control agent as compared to the competing microflora may also improve the efficacy of the biological control agent.

It is also important to note that certification of many species of unseasoned softwood lumber for pinewood nematode control will soon be required and that the proposed control method consists of steam pasteurization. Therefore, the present method for reducing sapstain can be readily incorporated into an existing method for eradicating pinewood nematodes.

While the above description relates to one embodiment of the present invention, it is to be appreciated that the method can be applied to various types of wood products including all types of soft wood lumber and woodchips. The biological control agent can be chosen from any agent that is effective in reducing the levels of sapstain in pasteurized wood. Fungi selected from the class Hyphomycetes have been demonstrated to be effective in this regard, including the genera Gliocladium (Seifert et al. 1988, Brevll et al. 1992), Trichoderma (Richard 1987, Motell and Sexton, 1992), Scytalidlum (Ricard 1987, Klingstrom and Johansson, 1973) and Mariannaea ( Seifert et al. 1993).

References BaoJun, Y. and W. Quouli, 1989. Distribution of pinewood nematodes in China and susceptibility of some Chinese and exotic pines to the nematodes. Can. J. Forbes. , 19(12) 1527–1530. Block, S. S. 1977. Disinfection, sterilization and preservation. 2nd ed. Lea & Febiger, Philadelphia. 1049 pp. Boyette, C. D. 1986. Evaluation of Alternaria crassa for biological control of Jimsonweed: Host range and virulence. Plant. Sci. 45: 223–228. Breuil, C., B. T. Luck, L. Rossignol, J. Little, C. J. Echeverrie, S. BanerJee and D. L. Brown, 1992. Monoclonal antibodies to *Gliocladium roseum*, a potential biological control fungus of sapstaining fungi in wood. Cartwright K. St. G. and W.PK. Findlay, 1958, Decay of lumber and its prevention, H. M. Stationary Office, London. Clark, J. E. and R. S. Smith 1990. Re-infection of pasteurized wood with fungi following storage. FORINTEK INTERNAL Report Project 1712 KO10. Colley, R. H. and C. T. Rumbold 1930. Relation between moisture content of the wood and blue stain in loblolly pine. J. Agr. Res. 41: 389–399. Croan S. C. and T. L. Highley 1990, Biological control of the blue stain fungus Ceratocystis coerulescens with fungal antagonists. Mat and Org. 25, 255–266. Daniel J. T., G. E. Templeton and J. Smith Jr. 1974. Control of aeschynomene sp. with Colletotrichim qleosporioldes penz f. sp. aeschynomene U.S. Pat. No. 3,849,104. Deloitte, Haskins & Sells, 1989. Econimic benefit assessment of anti-sapstain chemicals used in B.C. sawmills, Report prepared for Forestry Canada. Dwinell, L. D. 1990. Heat treating and drying southern pine lumber infested with pinewood nematodes. For. Prod. J., 4.0: (11/12)5356. Gilbert, P. G. 1988. Lumber Quality Protection Chemical Products used in B.C. sawmills and shipping terminals. Paper presented to the Whistler '88' Conference of the Air and Waste Management Association, Whistler, B. C. November, 1988. Hanssen H. W., N. D. Henderson and J. E. H. Ward. 1991. A review of the environmental impact and toxic effects of TCMTB, Environmental Protection Division, B.C. Environment ISBN 0-7726-1440-7. Harman, G. and R. D. Lumsden, 1990. Biological disease control, Pgs 259–279 in The Rhizosphere J. M. Lynch ed, John Wiley and Sons, Chichester.

Henderson, N. D. 1992, A review of the environmental impact and toxic effects of IPBC. Environmental Protection Division, B.C. Environment ISBN 0-7726-1603-2.

Jones, P. A. 1981, Chlorophenols and their impurities in the Canadian environment. Environmental Protection Service, Environment Canada, E.P.S.-3-EC-81-2.

Klingstrom, A. E. and S. M. Johansson, 1973. Antagonism of Scytalidium isolates against decay fungie. Phytopathology 63,473–479.

Lewis, J. A., D. Lumsden, G. Papavizas, M. Hollenbeck and J. F. Walker, 1991. Fungal formulation for biocontrol of soilborne plant pathogens. U.S. Pat. No. 5,068,105.

Mamiya, J. and T. Kiyohara. 1972. Description of *Bursaphelenchus lignicolous* n.sp. (Nematoda, aphelenchoididae) from pine wood and histophathology of nematode-infested trees. Nematologica, 18:120–124.

Miller, D. J. and J. J. Morrell. 1989. Controlling sapstaint trials of product group I on selected western softwoods, Research Bullet in 65, Forest Research Laboratory, Corvallis, Oreg.

Miller, D. J., J. J. Morrell and M. Mitchoff. 1990. Controlling sapstain; trials of product group II on selected western softwoods. Research Bulletin 66, Forest Research Laboratory, Corvallis, Oreg.

Morrell, J. J. and C. M. Sexton, 1992Effect of environmental variables on performance of bioprotectants against wood staining fungi, Paper presented at the Joint meeting of the American Phytophathological Society and the Mycological society of Americal, Portland, Oreg.

Mukhopadhyay, A. N., S. M. Shretha and P. K. MukkorJee 1992. Biological seed treatment for control of soil-borne plant pathogens FAO Plant Prot. Bull. 40:21–30

Nielsen, R. I. J. Breinholt and G. W. Jensen. 1992Fungicidally active compounds. International Patent Publication No. WO92/05191.

Ostaff, D. and M. Y. Cech. 1978. Heat sterilization of spruce-pine-fir lumber containing sawyer beetle larvae (Coleopetera: Cerambycidae, Monochamus sp.). East. For. Prod. Lab., Can. For. Serv., Ottawa, Rep. OPX200E. 9 pp.

Reyes A. A. 1984. Suppressive activity of different fungi against cabbage yellows in the soil and *Fusarium oxysporum* f.sp. conglutinans in vitro Phytoprotection 65: 27–33.

Ricard, J. L. 1987. Method of using immunizing commensals. U.S. Pat. NO. 4,678,669.

Rutherford,T. A., Y. Mamiya and J. M. Webster, 1990. Nematoide-induced induced pine wilt disease, factors influencing its occurrence and distribution. For. Science, 361:145–155.

Seifert, K. A. 1992. Sapstain of commercial lumber by species of Ophiostoma and Ceratocystis. Pgs 145–155 in Ceratocystis and Ophiostoma, Taxonomy, Ecology & Pathogenicity. American Phytopath-ological Society. Wingfield, M. J., Seifert, K. A. and Webber, J. F. eds.

Seifert, K. A., C. Breuil, L. Rossignol, M. Best and J. N. Saddler, 1988. Screening for microorganisms with the potential for biological control of sapstain on unseasoned lumber. Mat und Org. 23:81:95.

Seifert, K. A., C. Breuil, M. Mes-Hartree, L. Rossignol and B.C. Bilmer. 1993. Mariannaea elegans, an antagonist of sapstaining Ophiostoma species.

Soderstrom, O. 1986, Protection of coniferous saw logs in storage. A literature survey. The Swedish University of Agriculture Sciences, Dept. of Forest Products Report No. 179, 33 pgs. Sykes, G. 1965. Disinfection and sterilization. 2nd ed. E. & F.M. Spon Ltd. London, England. 486 pp.

Walker, H. L. 1983. Control of Prickly sida velvetleaf and spurred anoda with fungal pathogens. U.S. Pat. No. 4,419,120.

Wang, C. J. K. and R. A. Zabel, 1990. Identification manuel for fungi from utility poles in the eastern United States, American Type Culture Collection, Allen Press, Kans., 356 pgs.

The embodiments of the invention in which an exclusive property or privilidges is claimed are defined as follows:

1. A method for controlling sapstain in wood and wood products comprising:

a) steam pasteurizing the wood or wood product; and
   b) subsequently treating the wood or wood product with a biological control agent comprising one or more fungi selected from the class Hyphomycetes, wherein the efficacy of b) in controlling sapstain is greater when used in conjunction with a), relative to the use of b) alone.

2. The method according to claim 1 wherein said wood or wood product is pasteurized for a sufficient period of time such that the internal temperature of the wood reaches at least 56° C.

3. The method according to claim 2 wherein said wood or wood product is pasteurized for at least 30 minutes.

4. The method according to claim 1 wherein said fungi is selected from the genus Gliocladium.

5. The method according to claim 4 wherein said fungi is *Gliocladium aureum*.

6. The method according to claim 1 wherein said wood or wood product is softwood lumber.

7. The method according to claim 6 wherein said softwood lumber is hemfir lumber.

8. A wood or wood product treated according to the method of claim 1.

9. A wood or wood product treated according to the method of claim 2.

10. A wood or wood product treated according to the method of claim 3.

11. A wood or wood product treated according to the method of claim 4.

12. A wood or wood product treated according to the method of claim 5.

13. A wood or wood product treated according to the method of claim 6.

14. A wood or wood product treated according to the method of claim 7.

* * * * *